(12) United States Patent
Van der Ham et al.

(10) Patent No.: US 10,837,952 B2
(45) Date of Patent: Nov. 17, 2020

(54) METHOD AND APPARATUS FOR DETECTING A BEARING LUBRICATION FAILURE

(71) Applicant: AKTIEBOLAGET SKF, Gothenburg (SE)

(72) Inventors: Andreas Clemens Van der Ham, Utrecht (NL); Jeroen Bongaerts, Nieuwegein (NL); Gert-Jan Scheers, Nieuwegein (NL)

(73) Assignee: AKTIEBOLAGET SKF, Gothenburg (SE)

( * ) Notice: Subject to any disclaimer, the term of this patent is extended or adjusted under 35 U.S.C. 154(b) by 227 days.

(21) Appl. No.: 15/844,746

(22) Filed: Dec. 18, 2017

(65) Prior Publication Data
US 2019/0187122 A1    Jun. 20, 2019

(51) Int. Cl.
| | |
|---|---|
| *G01N 33/28* | (2006.01) |
| *G01M 13/04* | (2019.01) |
| *G01M 13/045* | (2019.01) |
| *F16C 33/66* | (2006.01) |

(52) U.S. Cl.
CPC ..... *G01N 33/2888* (2013.01); *F16C 33/6625* (2013.01); *G01M 13/04* (2013.01); *G01M 13/045* (2013.01); *F16C 33/6622* (2013.01); *F16C 33/6659* (2013.01); *F16C 2233/00* (2013.01)

(58) Field of Classification Search
CPC .................................................. F16C 33/6625
See application file for complete search history.

(56) References Cited

U.S. PATENT DOCUMENTS

| | | | | |
|---|---|---|---|---|
| 5,485,491 A | * | 1/1996 | Salnick .................. | G01R 31/34 376/245 |
| 6,339,961 B1 | * | 1/2002 | Goodman ............... | F16N 29/02 184/105.2 |

(Continued)

OTHER PUBLICATIONS

Donald Howieson, "Vibration Monitoring: Envelope Signal Processing Using Envelope Signal Processing in Vibration Monitoring of Rolling Element Bearings", pp. 1-14, Feb. 2003, Diagnostic Instruments, Livingston, Scotland.

*Primary Examiner* — Paul M. West
*Assistant Examiner* — Mark A Shabman
(74) *Attorney, Agent, or Firm* — J-Tek Law PLLC; Scott T. Wakeman; Mark A. Ussai

(57) ABSTRACT

A bearing lubrication system includes a lubricant distributor configured to perform a lubrication operation by moving lubricant toward an interior of a housing of a bearing, at least one sensor configured to measure at least one condition of the bearing and to produce a signal indicative of the at least one measured condition and a controller configured to produce a transient detection signal, a signal indicative of a second derivative of the measurement signal, for example, and to determine whether an absolute value of the transient detection signal exceeds a threshold value during a given time period after the lubrication operation and to output a failure signal indicative of a lubrication failure in response to a determination that the absolute value of the transient detection signal does not exceed the threshold value during the given time period. Also a method of operating a bearing lubrication system.

20 Claims, 4 Drawing Sheets

(56) References Cited

U.S. PATENT DOCUMENTS

| | | | | |
|---|---|---|---|---|
| 6,546,785 B1* | 4/2003 | Discenzo | ............... | F16C 19/52 73/53.05 |
| 2003/0115977 A1* | 6/2003 | Holweg | ............... | F16C 41/007 73/865.9 |
| 2004/0250623 A1* | 12/2004 | Walker | ................. | F16C 19/52 73/593 |
| 2008/0065354 A1* | 3/2008 | Yoshioka | ............... | F16C 29/00 702/183 |
| 2011/0265569 A1* | 11/2011 | Ganji | .................. | F16C 19/52 73/587 |

* cited by examiner

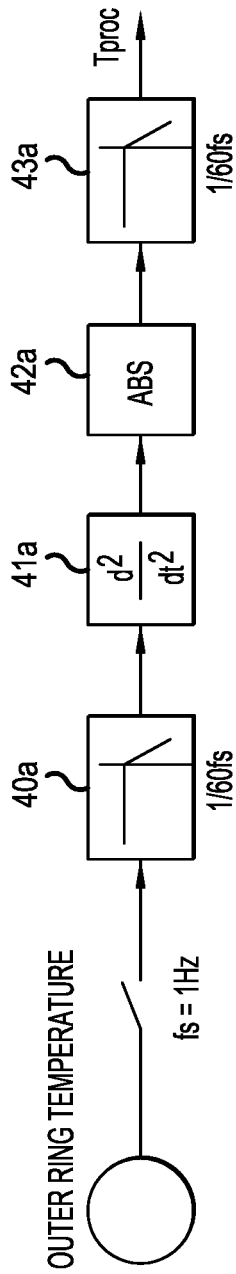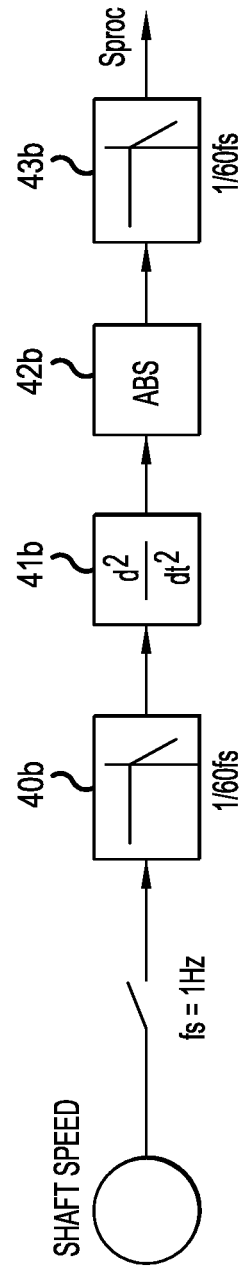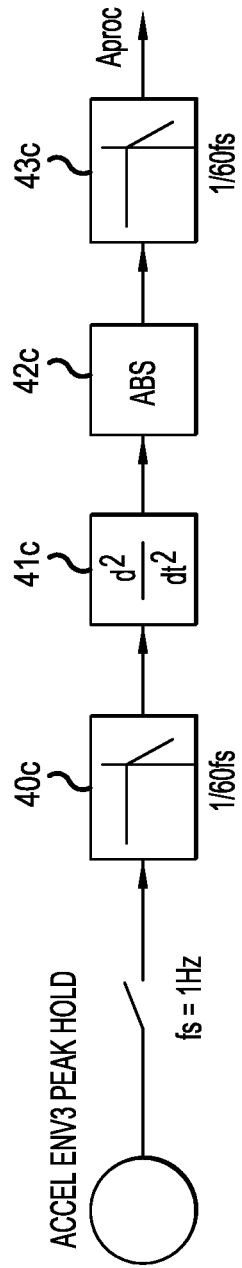

METHOD AND APPARATUS FOR DETECTING A BEARING LUBRICATION FAILURE

TECHNOLOGICAL FIELD

The present disclosure is directed to a method and apparatus for detecting a bearing lubrication failure, and, more specifically, toward a method and apparatus for detecting a bearing lubrication failure based on one or more signals indicative of a bearing temperature and/or a bearing speed and/or a bearing acceleration.

BACKGROUND

Many bearings require lubrication in order to ensure proper operation. Lubrication events may occur at set time periods, or lubrication intervals may be adjusted in response to a detected operating condition of the bearing, e.g., lubrication may occur more frequently at high temperatures and/or at high bearing speeds. Any suitable lubricant can be used for lubricating a bearing including oil and grease.

Many lubrication systems are known for providing bearings with lubricant, including, without limitation, single-line lubrication systems, dual-line lubrication systems, multi-line lubrication systems and progressive lubrication systems. In general, such systems operate by increasing the pressure of a quality of lubricant in a supply line in order to move that quantity of lubricant into a bearing housing or by opening a valve to allow an already-pressurized quantity of lubricant to enter the bearing housing. The movement may be caused by a pump, or by a spring, or by the movement of a piston; however the movement is caused, the intended result is that the lubricant, generally a predetermined measured quantity of the lubricant, moves through a lubrication supply line into a bearing housing and into contact with the wear surfaces of the bearing where wear and friction occur, namely, the bearing rolling elements and/or the bearing raceways, or, in the case of plain bearings, into contact with the mutually contacting slide surfaces of the bearings.

Unfortunately, not every lubrication event results in a necessary quantity of lubricant reaching the wear surfaces of the bearing. For example, if a lubricant supply line is broken or blocked, or if the lubricant is too thick (because, for example, it is too cold) the lubrication operation (pressure increase, valve opening, etc.) that would move lubricant to the bearing wear surfaces under normal conditions will not result in proper lubrication of the bearing. Monitoring the operation of a pump or the pressure of the lubricant in the supply line or the opening of a valve, therefore, is not sufficient to determine whether proper bearing lubrication is occurring.

One device for detecting a lubrication event is a flow meter. The flow meter can be configured to produce a signal when a movement of a predetermined quantity of the lubricant is detected. However, if there is a lubricant leak downstream from the location of the flow meter, the flow meter could indicate that a lubrication event was successful when, in fact, a necessary quantity of lubricant did not reach the relevant bearing elements.

Another hard-to-detect lubrication failure, one that cannot be detected by a flow meter, results from lubricant entering a bearing housing and accumulating at a location remote from the bearing wear surfaces. For example, if the lubricant is more viscous than desired, it may not move far from the location at which it enters the bearing housing. Instead, it may build up on an interior wall of the bearing housing near the lubrication opening into the housing. A flow meter would confirm that a flow of lubricant into the bearing housing had occurred, but it would not detect that the lubricant had failed to reach the bearing wear surfaces where it was needed.

It is important to detect lubrication failures or under-lubrication conditions rapidly in order to prevent bearing damage. Especially in systems configured to apply only the minimum amount of lubricant necessary for proper bearing operation, failing to detect even a small number of failed lubrication events can rapidly lead to bearing damage. Similarly, in systems where the movement of grease through a lubricated system is required in order to pump contaminants out of a bearing housing, system service life depends on a continuous flow of grease to the bearing, and even a small number of failed lubrication events may contribute to an early failure of a bearing.

It would therefore be desirable to more reliably detect failed bearing lubrication events.

SUMMARY

These problems and others are addressed by embodiments of the present disclosure, a first aspect of which comprises a method that includes measuring at least one condition of a bearing having at least one raceway and at least one rolling element in an interior of a housing. The method includes producing a measurement signal indicative of the at least one measured condition and producing a transient detection signal indicative of a transient in the measurement signal. The method further includes performing a lubrication operation that comprises moving a lubricant toward the interior of the housing or increasing a pressure of the lubricant in a supply line or opening a valve in a supply line, and determining whether an absolute value of the transient detection signal exceeds a threshold value during a given time period after the lubrication operation. The method also includes outputting a failure signal indicative of a lubrication failure in response to a determination that the absolute value of the transient signal does not exceed the threshold value during the given time period.

Another aspect of the disclosure comprises a bearing lubrication system that includes a lubricant distributor configured to perform a lubrication operation by moving lubricant toward an interior of a bearing housing of a bearing, which bearing has at least one raceway and at least one rolling element in an interior of the housing. The system includes at least one sensor configured to measure at least one condition of the bearing and to produce a signal indicative of the at least one measured condition, and the system includes a controller. The controller is configured to produce a transient detection signal indicative of a transient in the measurement signal and to determine whether an absolute value of the transient detection signal exceeds a threshold value during a given time period after the lubrication operation and to output a failure signal indicative of a lubrication failure in response to a determination that the absolute value of the transient detection signal does not exceed the threshold value during the given time period.

Still another aspect of the disclosure comprises a bearing lubrication system that includes means for measuring at least one condition of a bearing, the bearing having at least one raceway and at least one rolling element in an interior of a housing, means for producing a measurement signal indicative of the at least one measured condition, and means for producing a transient detection signal indicative of a transient in the measurement signal. The system also includes means for performing a lubrication operation at the bearing, the lubrication operation comprising moving a lubricant toward the interior of the housing or increasing a pressure of the lubricant in a supply line or opening a valve in a supply line, means for determining whether an absolute value of the transient detection signal exceeds a threshold value during a given time period after the lubrication operation, and means for outputting a failure signal indicative of a lubrication failure in response to a determination that the absolute value of the transient detection signal does not exceed the threshold value during the given time period.

BRIEF DESCRIPTION OF THE DRAWINGS

These benefits and others will be better understood after a reading of the following detailed description in connection with the attached drawings, wherein:

FIGS. 3a-3c are schematic circuit diagrams illustrating signal processing performed by the controller of FIG. 1.

DETAILED DESCRIPTION

Figure 1:
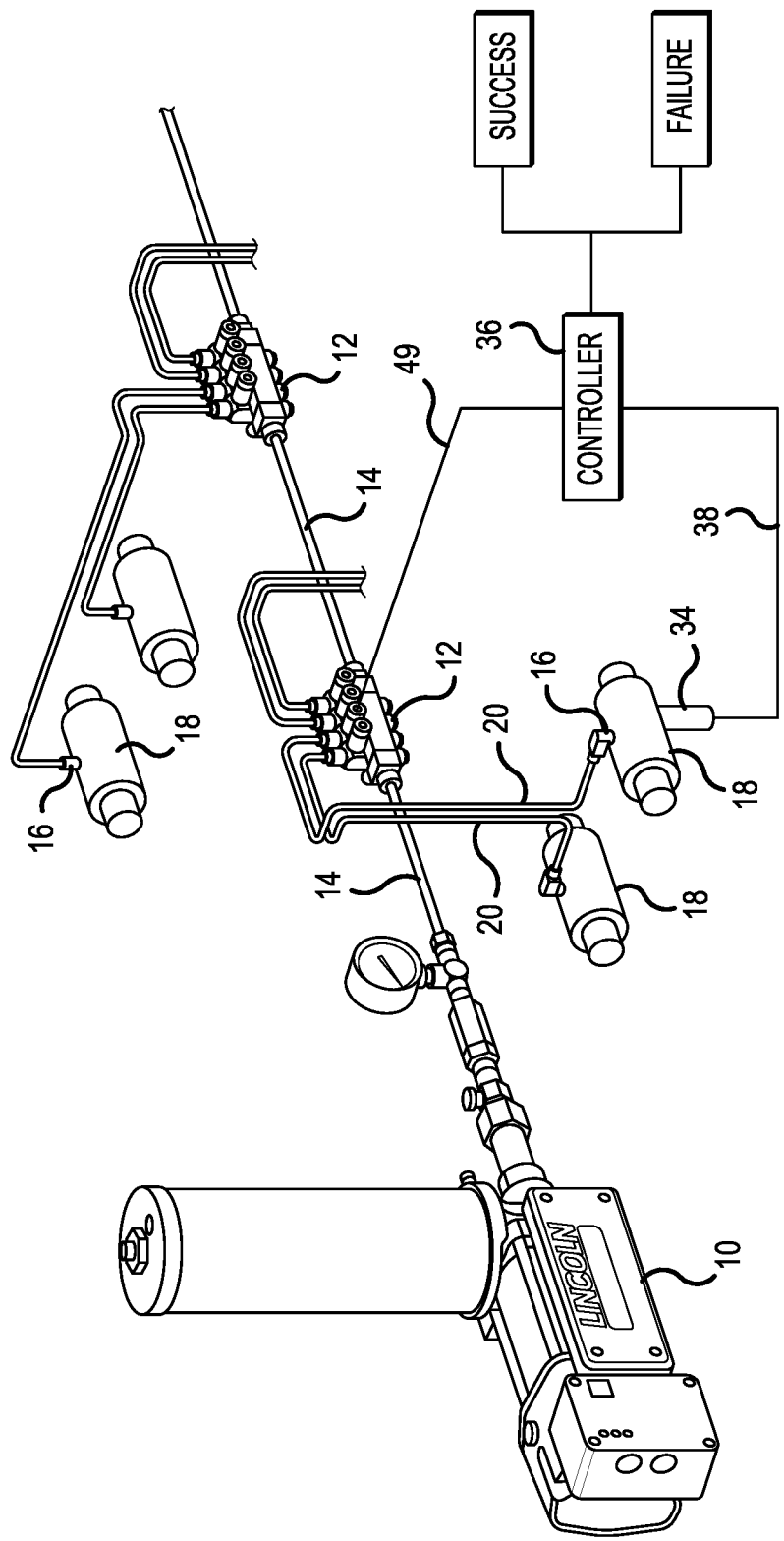
FIG. 1 is a schematic view of a lubrication system according to the present disclosure configured to provide lubricant to multiple locations including to a bearing housing which lubrication system includes a controller and a sensor.
Figure 2:
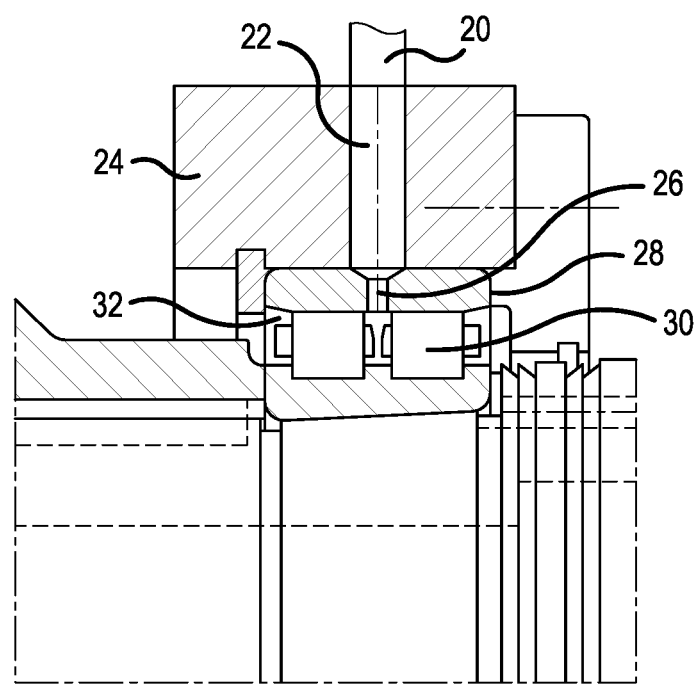
FIG. 2 is a side elevational view of a lubrication passage leading to a bearing in the housing of FIG. 1.

Referring now to the drawings, wherein the showings are for illustrating embodiments of the disclosure only and not for the purpose of limiting same, FIG. 1 shows a lubrication system according to the present disclosure that includes a lubrication pump 10 connected to first and second lubricant injectors 12 by feed lines 14. Each of the lubricant injectors 12 has four ports, and each of the ports is connected to a lubrication point 16 of a bearing 18 by a supply line 20. As shown in FIG. 2, each of the supply lines 20 connects to a first passageway 22 in a bearing housing 24 which is in fluid communication with a second passageway 26 in a bearing outer ring 28 so that the lubricant moves through the first passageway 22 and the second passageway 26 to reach the rolling elements 30 in the interior 32 of the bearing 18.

In a known manner, the lubrication pump 10 provides a lubricant such as grease to the lubricant injectors 12, and each of the lubricant injectors 12 includes metering valves (not illustrated) for dispensing precise quantities of grease to the lubrication points 16. The lubricant is dispensed to the lubrication points 16 in a conventional manner.

As used herein, an action intended to move a quantity of the lubricant to the wear or contact surfaces of a bearing is referred to herein as a "lubrication operation." If the lubrication operation results in a necessary quantity of lubricant reaching the bearing wear surfaces, it is considered a successful operation; if the lubrication operation does not result in the necessary quantity of the lubricant reaching the bearing wear surfaces, it is considered a failed operation.

A lubrication operation may comprise the opening of a valve in one of the lubricant injectors 12 or an increase in a pressure that, under normal circumstances, would move the lubricant toward the interior 32 of one of the bearings 18. In systems with a single pump for moving lubricant to a lubrication point, a lubrication operation may comprise an operation of the pump. When a lubrication operation is successful, a known amount of the lubricant reaches the bearing wear surfaces, that is, the mutually contacting surfaces where lubrication is required. However, various conditions can lead to a failed lubrication operation. These include a break in one of the supply lines 20, or the viscosity of the lubricant being too high such that, for example, opening a valve in the lubricant injector 12 does not result in the movement of a sufficient quantity of the lubricant to the wear surfaces. It is also possible that the lubricant will enter the bearing housing 24 and then accumulate at a side of the housing without reaching the bearing surfaces that require lubrication. Any one of these lubrication operation failures will leave a bearing with inadequate lubrication and may lead to the premature failure of the bearing.

In order to better detect failed lubrication operations and/or confirm successful lubrication operations, the present disclosure includes a sensor 34 connected to each of the bearings 16. The sensors 34 may be provided specifically for the purpose of detecting lubrication failures; however, more often, the sensors 34 are provided for other reasons and are therefore already present in a bearing lubrication system. These sensors 34, illustrated schematically, may detect one or more conditions of a bearing including a bearing temperature, a bearing speed and/or a processed bearing acceleration signal, such as enveloped acceleration or an enveloped peak hold (ENV3 peak hold) signal. In this context, it should be noted that "acceleration" represents bearing vibration, rather than a change in the rotational speed of the bearing. One sensor 34 may detect multiple ones of these conditions, or separate sensors 34 may be provided for sensing each of the conditions. The sensors 34 produce output signals indicative of the condition or conditions being measured, and those signals are transmitted to a controller 36 over a first output line 38. The controller 36 may comprise a microprocessor, an application-specific integrated circuit (ASIC), an integrated circuit (IC), a system-on-a-chip (SOC), a programmable logic element, or a field programmable gate array (FGPA) including a microprocessor. Instead of the first output line 38, signals could be sent wirelessly from the sensors 34 to the controller 36 without exceeding the scope of this disclosure.

The present inventors have found that a successful lubrication operation can be detected by looking for certain types of changes in one or more of the speed, temperature and acceleration signals. This is because shortly after the time that the lubricant reaches the contact or wear surfaces of the bearing there is a transient drop in the bearing speed and a transient drop in the acceleration enveloped level. There will also be a transient change in bearing temperature, the direction of which depends on the lubrication condition of the bearing. The transient changes in bearing speed and acceleration occur because the new lubricant, typically grease, entering the raceway increases friction which can reduce the bearing speed. The body of additional grease also damps vibrations, thereby causing a decrease in the enveloped acceleration level. As regards temperature transients, if the bearing is adequately lubricated, adding additional lubricant will cause a transient increase in bearing temperature due to the increased friction until the grease is smeared out evenly. If the bearing has been inadequately lubricated, on the other hand, a new dose of grease can cause a transient decrease in temperature when the cool grease reaches a hotter-than-normal bearing. Therefore, according to the present disclosure, information can be extracted from the temperature and/or speed and/or acceleration signals that provides a strong indication that a lubrication operation has failed or succeeded. Specifically, when transients are detected in the speed, temperature and acceleration signals at the same time, or at substantially the same time, within about thirty seconds of each other, for example, these transients provide a strong indication that a successful lubrication operation has occurred.

The temperature, speed and acceleration signals change over time for various reasons, and most of these changes are not related to lubrication operations. However, certain transients in these signals, that is, certain changes in one direction and then the other that occur sufficiently rapidly, are indicative of lubrication operations. Because the rate at which one or more of these signals changes is significant, the present disclosure considers second derivatives of one or more suitably processed measurement signals. This is discussed in greater detail below. However, even if a second derivative of a measurement signal is not specifically calculated, any signal that indicates a transient in a measurement signal, that is, a signal that indicates how quickly the measurement signal changes in one direction and then the other, is also considered a "signal indicative of a second derivative of a measurement signal" according to this disclosure.

Importantly, conventional controllers use the outputs of various sensors to monitor bearing operation and to look for conditions that may indicate bearing damage or bearing underlubrication. For example, if a bearing temperature sensor detects that the bearing temperature has increased above a given threshold, this may indicate that friction is increasing and that the bearing is not being adequately lubricated. Similarly, a bearing acceleration sensor may detect increased vibrations that indicates bearing damage, caused, for example, by underlubrication. A problem with such detection methods, however, is that they detect damage caused by bearing underlubrication rather than the underlubrication itself. That is, by the time the underlubrication has caused a temperature or vibration increase, damage to the bearing may already have occurred.

The controller 36 of the present disclosure is configured to determine whether a given lubrication operation has succeeded and/or failed before damage to the bearing occurs. This is accomplished by processing a bearing temperature signal and/or a bearing speed signal and/or a bearing acceleration signal from the sensor 34 as schematically illustrated in FIGS. 3a-3c. In the disclosed embodiment, the signals are measured at one sample per second, and the transients take several minutes. Therefore, the signals are filtered to 1/60th of the original sample rate using a 4th order Butterworth filter 40 (40a, 40b, 40c) in order to improve the signal-to-noise ratio of the signals. In order to register the transient or acceleration of the signals, the second derivative is taken by a second derivative circuit 41 (41a, 41b, 41c) and this signal is rectified by a rectification circuit 42 (42a, 42b, 42c) and filtered through a second low-pass filter 43 (43a, 43b, 43c). Second order high-pass filters and other transient detections methods known in the art could also be used.

In order to be able to evaluate the signal against a set threshold, the signals are enveloped by an enveloping circuit comprising the rectification circuits 42 and the second low pass filters 43, thereby creating an absolute level for the transient. By taking the absolute value (ABS) of the signal and low pass filtering the output, the envelope of the transient is determined.

The Accel ENV3 Peak Hold involves envelope signal processing, which is different from the aforementioned enveloping circuit. Envelope signal processing is a two-stage process. The first process involves band-pass filtering the time domain signal using a band pass filter that centers on the region of high frequency energy. The filtering process results in a series of spiky bursts of energy, which, in the case of the acceleration signals, are the impacts from the rolling elements hitting defects as the bearing rotates. The second stage of the process is passing this filtered time signal through an enveloper in order to extract the repetition rate of the spiky bursts of energy. The enveloper is an electronic circuit that demodulates or rectifies the signal. What is extracted is the repetition rate of these spiky signals. If the FFT (fast Fourier transform) spectrum of this enveloped signal is then taken, it displays the bearing characteristic frequencies and their harmonics.

The controller 36 also receives a lubrication operation signal, that is, a signal indicating that a lubrication operation has occurred, from the lubricant injectors 12 on a second output line 49. Only one lubricant injector 12 and one sensor 34 are shown as being connected to the controller 36 in the drawings; however, it should be understood that all sensors 34 and all lubrication injectors 12 can be connected to the controller 36, and that the controller 36 can be configured to provide an indication as to whether a lubrication operation has succeeded or failed for each lubrication point 16.

Figure 4A:
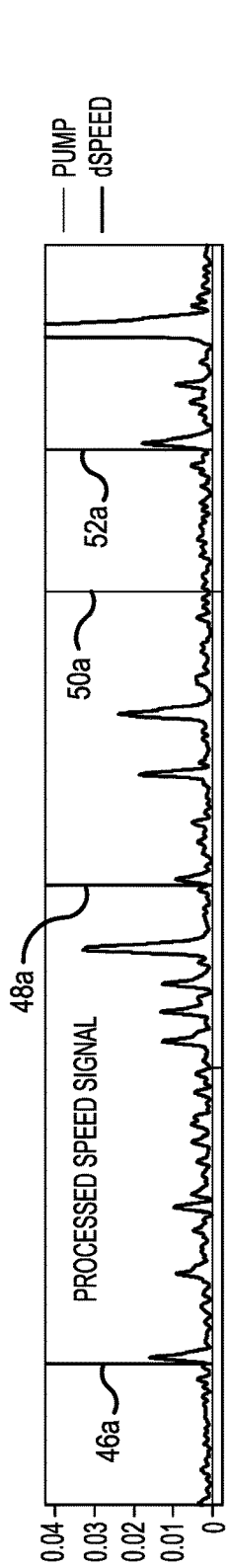
FIGS. 4a-4c are diagrams showing the processed signals produced by the circuits of FIGS. 3a-3c, respectively.
Figure 4B:
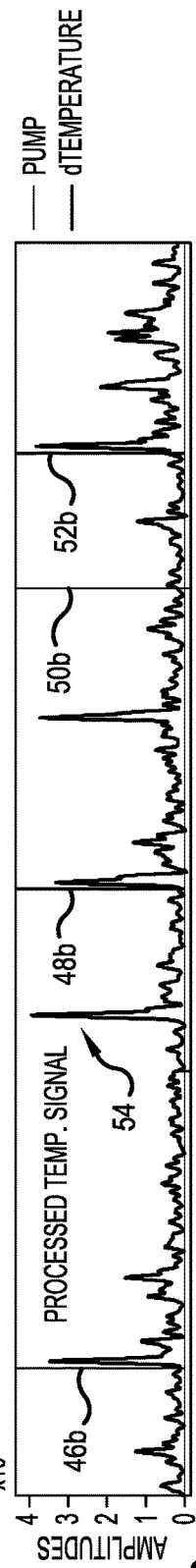
Figure 4C:
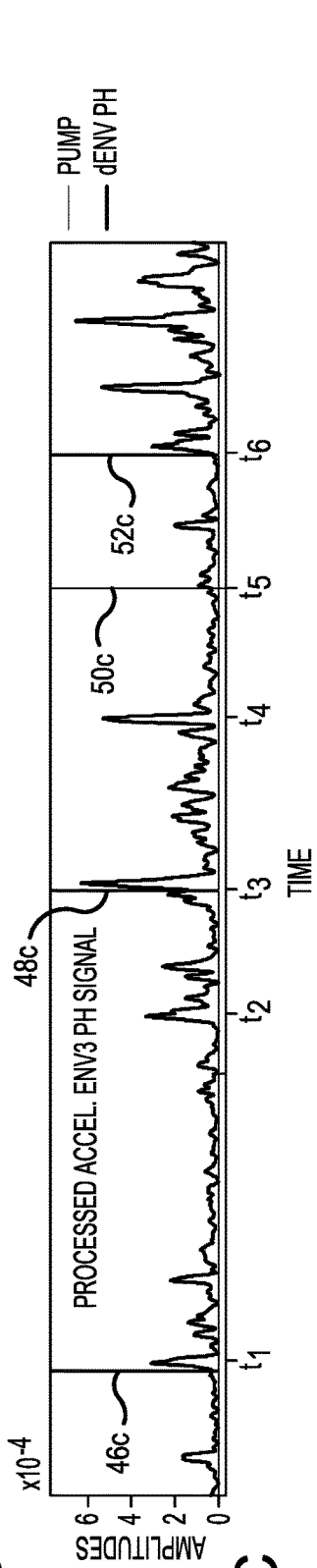

The results of this signal processing are illustrated in FIGS. 4a-4c which Figures also includes vertical lines 46, 48, 50 and 52 that show when first, second, third and fourth lubrication operations have occurred based on the signals received on the second output lines 49. The suffixes "a," "b," and "c" are added to reference numerals 46, 48, 50 and 52 to refer to lines in individual ones of the Figures. The operation of the disclosed lubrication system is discussed below in connection with FIGS. 4a-4c.

FIG. 4a illustrates the bearing speed signal processed by the circuit illustrated in FIG. 3a. The x-axis represents time and the y-axis represents the amplitude of the processed speed signal. The units on the y-axis in FIG. 4a range from 0 to 0.04; however, the units used are not of particular importance—only the threshold that must be exceeded in order to indicate a successful lubrication operation is important. In the present example, the threshold that must be exceeded to indicate a successful lubrication operation will be assumed to be 0.01; the precise threshold can be established empirically for particular bearings or types of bearings by observing the typical speed response to a lubrication operation for a given bearing. The threshold for the processed temperature signal of FIG. 4b that indicates a successful lubrication operation will be assumed to be 3, and the threshold for the processed enveloped acceleration signal will be assumed to be 2.

As will be appreciated from FIG. 4a, a lubrication operation occurs at time t1 as shown by line 46a, and a transient in the processed speed signal occurs within a given time, 5 minutes, for example, after the lubrication operation. A similar transient is observed at time t6 after line 52a which line represents another lubrication operation. It can therefore reasonably be assumed that the lubrication operations caused the temperature transients and that the lubrication operations were successful. However, as illustrated by line 48a in FIG. 4a, the temperature transient after the lubrication operation that occurred at time t3 did not reach the threshold of 0.01. Therefore, while temperature transients can provide useful information regarding the success or failure of a lubrication operation, additional confidence can be obtained by looking for transients in more than one of the processed signals.

FIG. 4b shows transients in the processed temperature signal that occur at times t1, t3 and t6 after lines 46b, 48b and 52b. However another transient at time t2, identified by reference numeral 54, is not associated with a lubrication operation. Considering the processed temperature signal alone therefore also provides useful information about the success or failure of a lubrication operation, but more reliable information can be obtained by looking for transients in multiple processed signals.

Finally, FIG. 4c shows transients in the processed acceleration enveloped signal. Here, transients are detected after lines 46c, 48c and 52c confirming that the lubrication operations indicated by lines 46c, 48c and 52c at times t1, t3 and t6 successfully moved lubricant into contact with the bearing wear surfaces.

No lubrication operation occurred at time t5; however, lines 50a, 50b and 50c were added to the data to provide an example of what would be observed in the event of a failed lubrication operation, for example, if a break occurs in the supply line leading to the bearing 18. In this case, the controller 36 would receive a lubrication operation signal at time t5 and monitor one or more of the processed speed signal, processed temperature signal and processed acceleration enveloped signal looking for transients. When, after 5 minutes, for example, no transients exceeding the predefined thresholds are observed, the controller 36 will produce an output signal to indicate a lubrication failure. Depending on the level of confidence required, it is also possible to output a lubrication failure signal only after two, three or another number of failed lubrication operations are detected. This failure signal may comprise, for example, an alarm or a warning light that illuminates or a warning on a display screen associated with the system being monitored.

Preferably, a determination regarding the success or failure of a given lubrication operation will be made after looking for transients in processed temperature, speed and acceleration enveloped signals. This would be done, for example, in systems that already provide temperature, speed and enveloped acceleration sensors for other reasons. However, in the event that a given bearing system only provides one or two relevant sensors, the present method can also be practiced with one or two such signals, albeit with a somewhat lesser level of confidence that every failed lubrication operation has been detected.

Similarly, even when a given lubrication system provides temperature, speed, and acceleration signals, the number of these signals in which transients are detected simultaneously (or substantially simultaneously, within about thirty seconds of one another, for example) can be used to provide a level of confidence that a lubrication event has succeeded. For example, if a transient is detected only in the temperature signal, this may provide a suggestion of a successful lubrication operation. However, if no transients occur at substantially the same time in the speed and/or acceleration signals, this may indicate that the temperature transient was not related to a successful lubrication operation. When transients are detected at substantially the same time in two of the three signals, this provides a stronger indication that a successful lubrication operation has occurred. The strongest indication of a successful lubrication operation is provided by the substantially simultaneous detection of transients in all three signals. Thus, it may be desirable to provide a warning signal each time only one transient occurs after a lubrication operation to indicate a possible failed lubrication operation and to provide an alarm signal each time no transients occur after a lubrication operation to indicate a high likelihood of a failed lubrication operation. A counter may also be provided to keep track of the number of times only one or only two substantially simultaneous transients are detected after a lubrication event.

It is noted that transients occur in all three processed signals at time t4. The inventors believe that the signals produced at time t4 represent a lubrication avalanche condition (a similar event may also have occurred at time t2). A lubrication avalanche occurs when lubricant builds up inside a bearing housing at a location remote from the bearing surfaces and then later breaks free. When such an event occurs at a time more than 5 minutes after a lubrication operation, it does not affect the disclosed method of detecting failed lubrication operations. If a lubrication avalanche occurs, coincidently, within five minutes of a lubrication operation, it is likely caused by the injection of new lubricant and also does not provide a false positive (because lubricant has reached the bearing wear surfaces).

Depending on certain implementation requirements, exemplary embodiments of the invention, such as the controller 36 and may be implemented in hardware and/or in software. The implementation can be performed using a digital storage medium, for example a ROM, a RAM, a PROM, an EPROM, an EEPROM or a flash memory, on which electronically readable control signals are stored, which interact or can interact with a programmable hardware component such that the respective method is performed.

The digital storage medium can therefore be machine- or computer readable. Some exemplary embodiments thus comprise a data carrier or non-transient computer readable medium which includes electronically readable control signals capable of interacting with a programmable computer system or a programmable hardware component such that one of the methods described herein is performed. An exemplary embodiment is thus a data carrier (or a digital storage medium or a non-transient computer-readable medium) on which the program(s) for performing one of the methods described herein is (are) recorded.

In general, exemplary embodiments of the present teachings may be implemented as a program, firmware, computer program, or computer program product including a program, or as data, wherein the program code or the data is operative to perform one of the methods if the program runs on a processor (e.g., a microprocessor) or other programmable hardware component. The program code or the data can for example also be stored on a machine-readable carrier or data carrier. The program code or the data can be, among other things, source code, machine code, bytecode or another intermediate code.

A program according to an exemplary embodiment can implement one of the methods during its performance, for example, such that the program reads storage locations or writes one or more data elements into these storage locations, wherein switching operations or other operations are induced in transistor structures, in amplifier structures, or in other electrical, optical, magnetic components, or components based on another functional principle. Correspondingly, data, values, sensor values, or other program information can be captured, determined, or measured by reading a storage location. By reading one or more storage locations, a program can therefore capture, determine or measure sizes, values, variable, and other information, as well as cause, induce, or perform an action by writing in one or more storage locations, as well as control other apparatuses, machines, and components, and thus for example also perform complex processes using displays, projectors, etc.

The present invention has been disclosed in terms of one or more embodiments. Additions and improvements to these embodiments will be recognized by persons of ordinary skill in the art upon a reading of the foregoing description. It is intended that all such modifications and additions form a part of the present disclosure to the extent they fall within the scope of the several claims appended hereto.

What is claimed is:

1. A method comprising:
measuring at least one condition of a bearing, the bearing having at least one raceway and at least one rolling element in an interior of a housing;
producing a measurement signal indicative of the at least one measured condition;
producing a transient detection signal indicative of a transient in the measurement signal;
performing a lubrication operation, the lubrication operation comprising moving a lubricant toward the interior of the housing or increasing a pressure of the lubricant in a supply line or opening a valve in a supply line;
determining whether an absolute value of the transient detection signal exceeds a threshold value during a given time period after the lubrication operation; and
outputting a failure signal indicative of a lubrication failure in response to a determination that the absolute value of the transient signal does not exceed the threshold value during the given time period.

2. The method according to claim 1, wherein the transient detection signal is a signal indicative of a second derivative of the measurement signal.

3. The method according to claim 2, wherein the at least one measured condition is one or more measured conditions selected from the group consisting of: a bearing temperature, a bearing speed and a bearing acceleration.

4. The method according to claim 2, wherein the at least one measured condition of the bearing is a bearing temperature.

5. The method according to claim 2, wherein the at least one measured condition is a bearing speed.

6. The method according to claim 2, wherein the at least one measured condition is a bearing acceleration.

7. The method according to claim 2, wherein the at least one measured condition is an enveloped acceleration peak hold signal.

8. The method according to claim 2, including, before producing the second derivative signal, filtering the measurement signal, the method further including rectifying the second derivative signal and filtering the rectified second derivative signal, thereby enveloping the second derivative signal.

9. The method according to claim 2, wherein the at least one measured condition is a bearing temperature and a bearing speed and a bearing acceleration.

10. The method according to claim 2, including outputting a success signal indicative of a successful lubrication operation in response to a determination that the absolute value of the second derivative signal exceeds the threshold value within the given time.

11. A bearing lubrication system comprising:
a lubricant distributor configured to perform a lubrication operation by moving lubricant toward an interior of a bearing housing of a bearing, the bearing having at least one raceway and at least one rolling element in an interior of the housing;
at least one sensor configured to measure at least one condition of the bearing and to produce a signal indicative of the at least one measured condition; and
a controller configured to produce a transient detection signal indicative of a transient in the measurement signal and to determine whether an absolute value of the transient detection signal exceeds a threshold value during a given time period after the lubrication operation and to output a failure signal indicative of a lubrication failure in response to a determination that the absolute value of the transient detection signal does not exceed the threshold value during the given time period.

12. The bearing lubrication system according to claim 11, wherein the transient detection signal is a signal indicative of a second derivative of the measurement signal.

13. The bearing lubrication system according to claim 12, wherein the at least one measured condition is one or more measured conditions selected from the group consisting of: a bearing temperature, a bearing speed and a bearing acceleration.

14. The bearing lubrication system according to claim 12, wherein the at least one measured condition of the bearing is a bearing temperature.

15. The bearing lubrication system according to claim 12, wherein the at least one measured condition is a bearing speed.

16. The bearing lubrication system according to claim 12, wherein the at least one measured condition is a bearing acceleration.

17. The bearing lubrication system according to claim 12, wherein the at least one measured condition is a bearing temperature and a bearing speed and a bearing acceleration.

18. A bearing lubrication system comprising:
means for measuring at least one condition of a bearing, the bearing having at least one raceway and at least one rolling element in an interior of a housing;
means for producing a measurement signal indicative of the at least one measured condition;
means for producing a transient detection signal indicative of a transient in the measurement signal;
means for performing a lubrication operation at the bearing, the lubrication operation comprising moving a lubricant toward the interior of the housing or increasing a pressure of the lubricant in a supply line or opening a valve in a supply line;
means for determining whether an absolute value of the transient detection signal exceeds a threshold value during a given time period after the lubrication operation; and
means for outputting a failure signal indicative of a lubrication failure in response to a determination that the absolute value of the transient detection signal does not exceed the threshold value during the given time period.

19. The bearing lubrication system according to claim 18, wherein the transient detection signal is a signal indicative of a second derivative of the measurement signal and wherein the means for measuring comprises one or more sensors selected from the group consisting of a bearing temperature sensor, a bearing speed sensor and a bearing acceleration sensor.

20. The bearing lubrication system according to claim 19, wherein the means for performing a lubrication operation at the bearing comprises a lubrication distributor.

* * * * *